United States Patent
Redmond

(10) Patent No.: US 6,536,974 B2
(45) Date of Patent: Mar. 25, 2003

(54) EASY OPENING LOW COST SWAB MEANS FOR APPLYING FLUIDS TO SURFACES

(75) Inventor: Sanford Redmond, Stamford, CT (US)

(73) Assignee: Sanford Redmond, Inc., Bronx, NY (US)

( * ) Notice: Subject to any disclaimer, the term of this patent is extended or adjusted under 35 U.S.C. 154(b) by 0 days.

(21) Appl. No.: 09/826,090

(22) Filed: Apr. 5, 2001

(65) Prior Publication Data
US 2001/0036384 A1 Nov. 1, 2001

Related U.S. Application Data

(60) Provisional application No. 60/194,824, filed on Apr. 5, 2000, and provisional application No. 60/212,977, filed on Jun. 21, 2000.

(51) Int. Cl.[7] .................................................. B43K 5/14
(52) U.S. Cl. ........................... 401/133; 401/132; 604/1; 604/3
(58) Field of Search ................................. 401/132, 133, 401/134, 135; 604/1, 2, 3; 222/541.3, 541.4, 541.6

(56) References Cited

U.S. PATENT DOCUMENTS

| 3,482,920 | A | * | 12/1969 | Schwartzman | 401/132 |
|---|---|---|---|---|---|
| 3,519,364 | A | | 7/1970 | Truhan | |
| 3,768,916 | A | * | 10/1973 | Avery | 401/132 |
| 3,986,640 | A | | 10/1976 | Redmond | 222/92 |
| 4,218,155 | A | * | 8/1980 | Weidner | 401/132 |
| 4,430,013 | A | * | 2/1984 | Kaufman | 401/132 |
| 4,493,574 | A | | 1/1985 | Redmond et al. | 401/132 |
| 4,611,715 | A | | 9/1986 | Redmond | 206/484 |
| 4,620,648 | A | | 11/1986 | Schwartzman | 222/490 |
| 5,472,112 | A | * | 12/1995 | Maciejewski | 220/745 |
| 5,490,736 | A | * | 2/1996 | Haber et al. | 401/132 |
| 5,681,574 | A | | 10/1997 | Haber et al. | |
| 5,772,346 | A | * | 6/1998 | Edwards | 401/132 |
| 5,775,826 | A | | 7/1998 | Miller | |
| 5,791,801 | A | * | 8/1998 | Miller | 401/132 |
| 6,062,413 | A | | 5/2000 | Redmond | 220/266 |
| 6,299,012 | B1 | | 10/2001 | Redmond | 220/266 |

FOREIGN PATENT DOCUMENTS

| GB | 1562640 A | 3/1980 |
|---|---|---|
| GB | 2233 886 A | 1/1991 |
| WO | WO 81/00196 | 2/1981 |
| WO | WO 98/11852 | 3/1998 |
| WO | WO 00/66371 | 11/2000 |

* cited by examiner

Primary Examiner—David J. Walczak
(74) Attorney, Agent, or Firm—Kenyon & Kenyon

(57) ABSTRACT

A swab (10) for applying fluids to a surface having a quick, easy opening dispenser package portion (12 and 14) and at least one sponge-like member (30). The dispenser package portion (12 and 14) includes a wall (12) made from a thermoplastic material and having an outlet creating formation (20). When a sufficient force is applied to the at least one outlet creating formation (20), an outlet opening (18) is formed allowing a release of the fluid contents (17) to flow from the dispenser package (12 and 14) and into the overlying at least one sponge-like member (30).

8 Claims, 10 Drawing Sheets

EASY OPENING LOW COST SWAB MEANS FOR APPLYING FLUIDS TO SURFACES

This application claims the benefit of U. S. Provisional Application No. 60/194,824, filed Apr. 5, 2000, and U. S. Provisional Application No. 60/212,977, filed Jun. 21, 2000. The complete disclosure of each Provisional Application is herein incorporated by reference.

FIELD OF THE INVENTION

The invention disclosed relates to dispenser packages and more particularly relates to easy opening, self-containing, easy to use, single use swabs.

BACKGROUND

The need for the application of fluids to surfaces runs the gamut from coating the skin with providone iodine or other antiseptics during surgery and births to the application of stains to wood or solvents to clean metal or plastic surfaces, as well as cosmetic fluids to remove or apply make-up, etc.

In the medical field, various complicated costly plastic units having frangible glass capsules containing providone iodine which are crushed by various means to release the fluid antiseptic into a sponge are presently used. In the low cost area, the swabs are invariably annoying to use; often getting contained products on the users hands and fingers.

SUMMARY

The invention relates to dispenser packages and more particularly relates to easy opening, fluid containing, easy to use, single use swab means for applying fluids to a surface. The swab means of the present invention is a simple unit comprising a quick, easy opening dispenser package portion to contain the fluid and at least one sponge-like member. The dispenser package portion includes a side wall made from a thermoplastic film and has an outlet creating formation thermoformed into it. The outlet creating formation comprises at least one hollow plastic formation and/or a breakaway tip member or protrusion extending from a surface of the wall wherein a locus of a line of intersection of a wall of the hollow plastic formation and/or breakaway tip member or protrusion with the surface of the side wall comprises a locus of a fault line. At least one sponge member is disposed adjacent to an exterior surface of the dispenser package wall in such a manner as to cover the outlet creating formation. When a sufficient force such as a quick squeeze between the thumb and the forefinger, for example, is applied to the at least one outlet creating formation, an outlet opening is formed permitting a release of the fluid contents to flow from the dispenser package on and into the overlying at least one sponge member.

In one embodiment, the at least one outlet creating formation comprises a thermoformed scored frangible plastic formation. When a sufficient force is applied to the said scored frangible plastic formation, as described above, it is broken along said fault lines. Once the frangible plastic formation member has been broken along said scored fault lines, an outlet opening is created through the at least one wall for the fluid contents of the dispenser package portion to flow into the adjacent at least one sponge member covering said outlet. Additionally, the frangible plastic formation member may comprise the entire container.

In another preferred embodiment, the at least one outlet creating formation comprises a breakaway plastic tip member. When a sufficient force is applied to the breakaway plastic tip member, described above, the breakaway plastic tip member is broken from the at least one wall of the dispenser package. Once the breakaway plastic tip member has been broken from the at least one wall, an outlet opening is formed for the fluid contents of the dispenser package portion to flow into the adjacent at least one sponge member. It is preferred that the breakaway tip member has the same or similar construction as any one of the breakaway tips disclosed in earlier filed and related non-provisional U.S. application Ser. No. 08/788,713, filed Jan. 23, 1997, and now U.S. Pat. No. 6,062,413, issued May 16, 2000, the disclosure of which is herein incorporated by reference.

It will be appreciated by those skilled in the art that the foregoing various brief descriptions and the following detailed description are exemplary and explanatory of the present invention, but are not intended to be restrictive thereof or limiting of the advantages which can be achieved by the invention or various combinations thereof The accompanying drawings referred to herein and constituting in part hereof, illustrate preferred embodiments of the invention and, together with the detailed description, serve to explain the principles of the invention.

DETAILED DESCRIPTION

Figure 2:
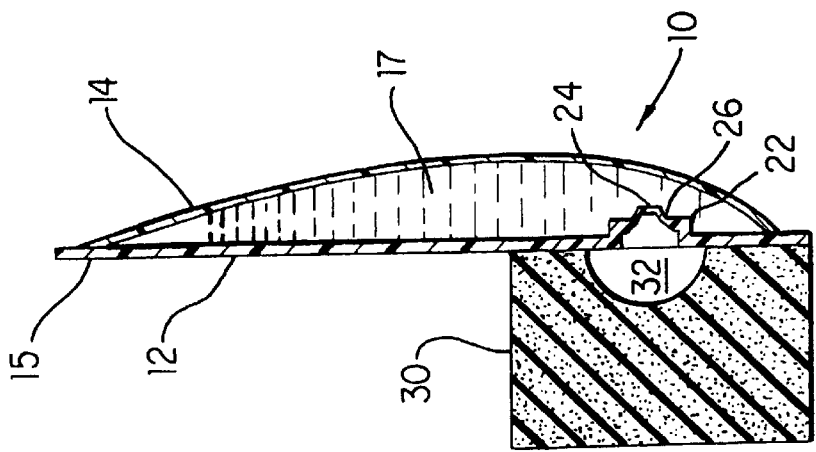
FIG. 2 is a cross-sectional side view of a swab constructed in accordance with the present invention.

Referring now to the drawings, where like reference numerals depict like elements, preferred embodiments of the present invention will be described below.

Figure 1:
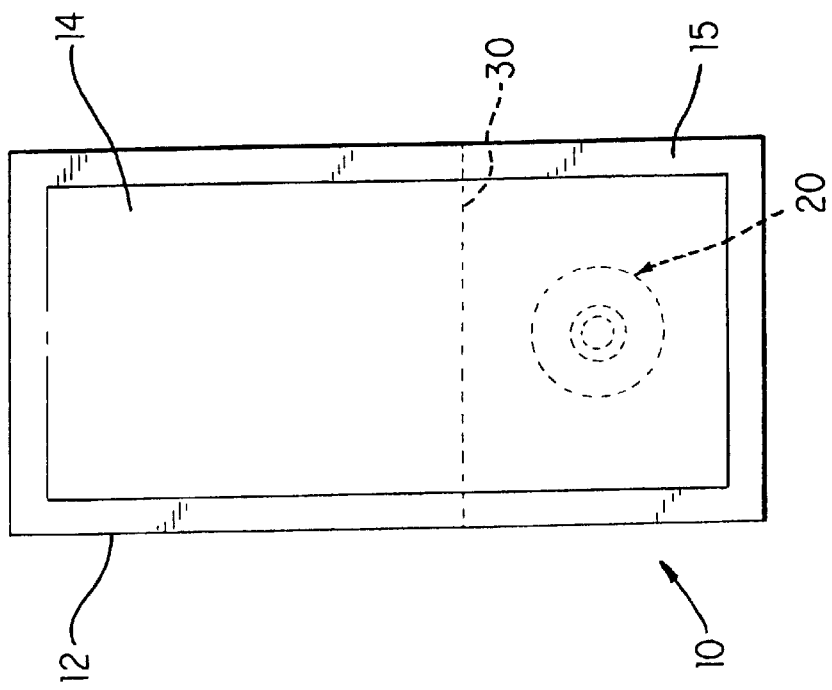
FIG. 1 is a plan view of a swab constructed in accordance with the present invention.
Figure 3:
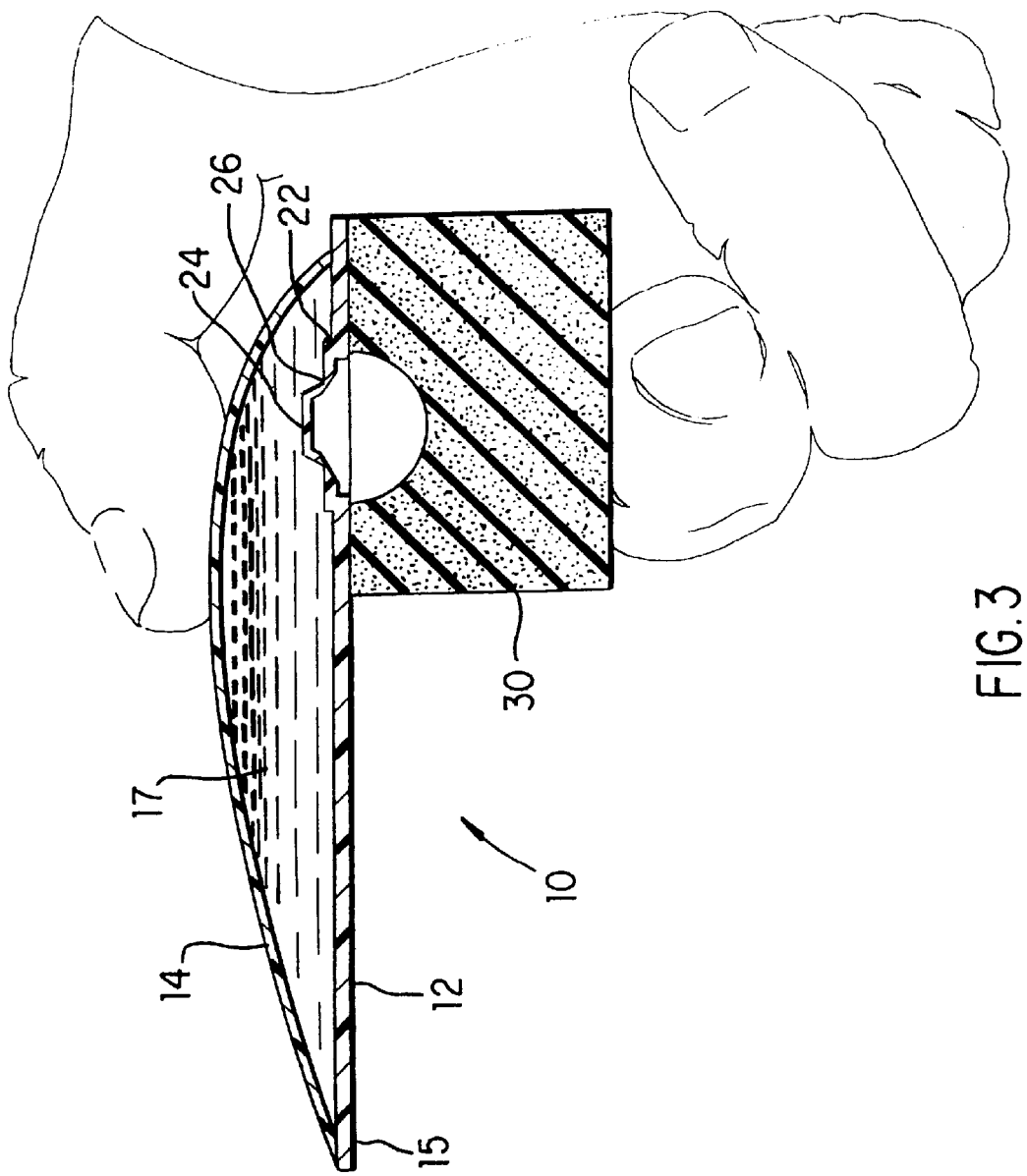
FIG. 3 is a cross-sectional side view of a swab constructed in accordance with the present invention prior to a sufficient breaking and/or crushing force being applied.

Referring more particularly to FIGS. 1–4, 7, and 9–12 of the accompanying drawings, there is illustrated a swab 10 generally at FIGS. 1 and 2 according to the present invention. The swab 10 is generally used for a single use, but in some circumstances, such as when used for non-medical purposes, for example, applying stain to wood, the swab 10 may be stored for later reuse.

As illustrated throughout the Figures, where like reference numerals indicate like elements, the swab 10 includes at least one wall member 12 formed from a flexible but relatively stiff sheet of a thermoformable plastic film most suitable to the product contained and the protection that the contained product requires. The embodiments illustrated in FIGS. 1–4 and 7–9 include a single, generally flat wall member 12. The embodiment illustrated in FIGS. 12 and 13, include at least one non-flat wall member 12. A more detailed discussion of types of thermoformable plastic materials used for the fabrication of flat and non-flat wall members 12 may be found in previously incorporated U.S. Pat. No. 6,062,413.

In accordance with the present invention and as illustrated in FIGS. 1–4 and 7–9, swab 10 includes a thin soft plastic side wall 14 bonded to the flexible, but relatively stiff wall member 12. The soft plastic side wall 14 and the wall member 12 are sealed together about their peripheries, generally shown at 15, to form a dispenser package portion of the swab 10 for containing a flowable fluid, generally shown at 17. The soft side wall 14 may be fabricated from any plastic material suitable to contain the product and the barrier protection that the contained product requires.

As shown in FIGS. 1–4 and 7, the relatively stiff generally flat wall 12 includes an outlet creating formation 20 which may include a base member 22 and a breakaway tip member 24 so that, upon breaking away of tip 24, an outlet opening in wall 12 is created through which the fluid contents 17 of the dispenser package may be dispensed.

Figure 4:
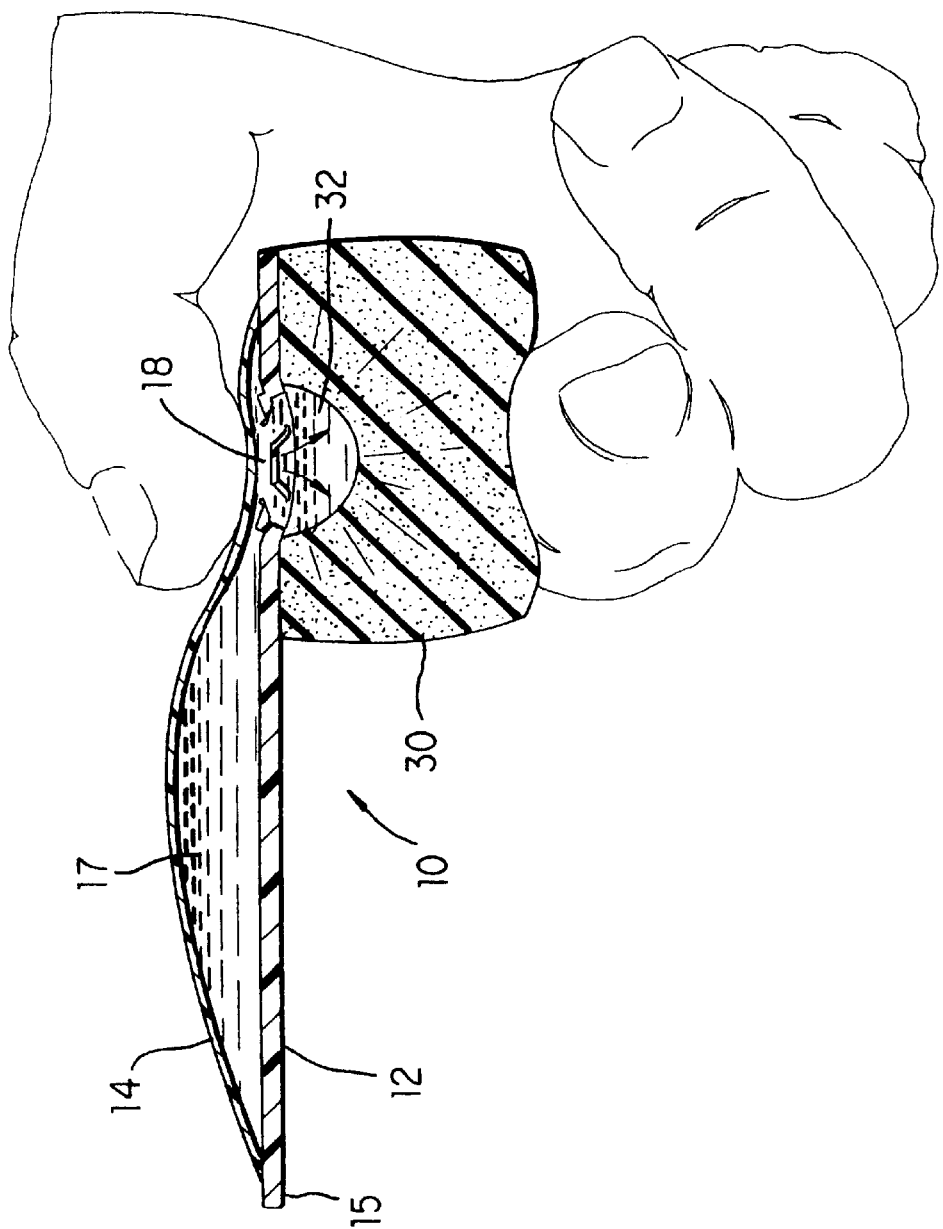
FIG. 4 is a cross-sectional side view of a swab in accordance with the present invention after a sufficient breaking and/or crushing force has been applied but not yet been released.
Figure 7:
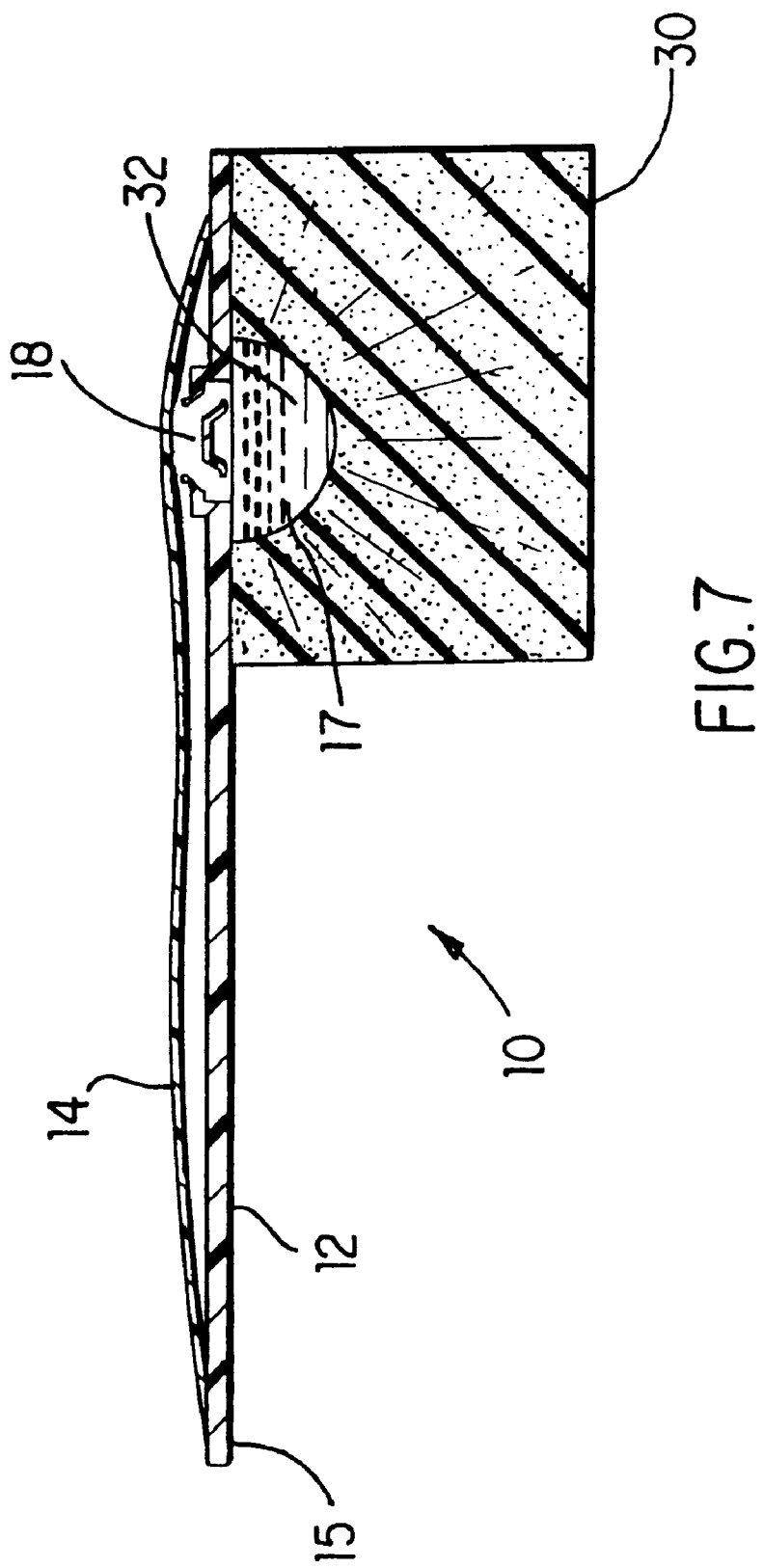
FIG. 7 is a cross-sectional side view of a swab in accordance with the present invention after a sufficient breaking force has been applied and released.

Swab 10, as shown in FIGS. 1–4 and 7–9, also includes a sponge-like member, or other suitable absorbent material (sponge member) 30 disposed adjacent to wall 12 and covers the outlet creating formation 20. The sponge member 30 extends along at least a portion of the area of the exterior surface of the wall 12. While the sponge member may be illustrated as being rectangular in cross-section, the sponge member 30 may be formed in any shape necessary for carrying out the function of the disclosed invention. Although not illustrated, it will be understood by those having ordinary skill in the art that the sponge member 30 may be disposed along any portion of the area of the exterior surface of the wall 12, including the entire area, as long as the sponge member 30 is positioned covering the outlet creating formation 20 so that when the breakaway tip 24 is broken away, forming outlet opening 18, the fluid contents 17 of the dispenser package flow into the sponge member 30. Additionally, the sponge member 30 may include a cavity 32 in the overlying vicinity of the outlet creating formation 20 for aiding a user in creating outlet opening 18, as shown in FIGS. 4, 7, and 8, and the flow of fluid contents 17 to and through outlet opening 18 and into sponge member 30. It should be understood that cavity 32 may be made of any shape and size necessary to carry out the function of the invention, including the use of no cavity at all. The sponge material 30 may be fabricated from any absorbent material suitable to the product contained and to the product's requirements for acceptable application.

Figure 5:
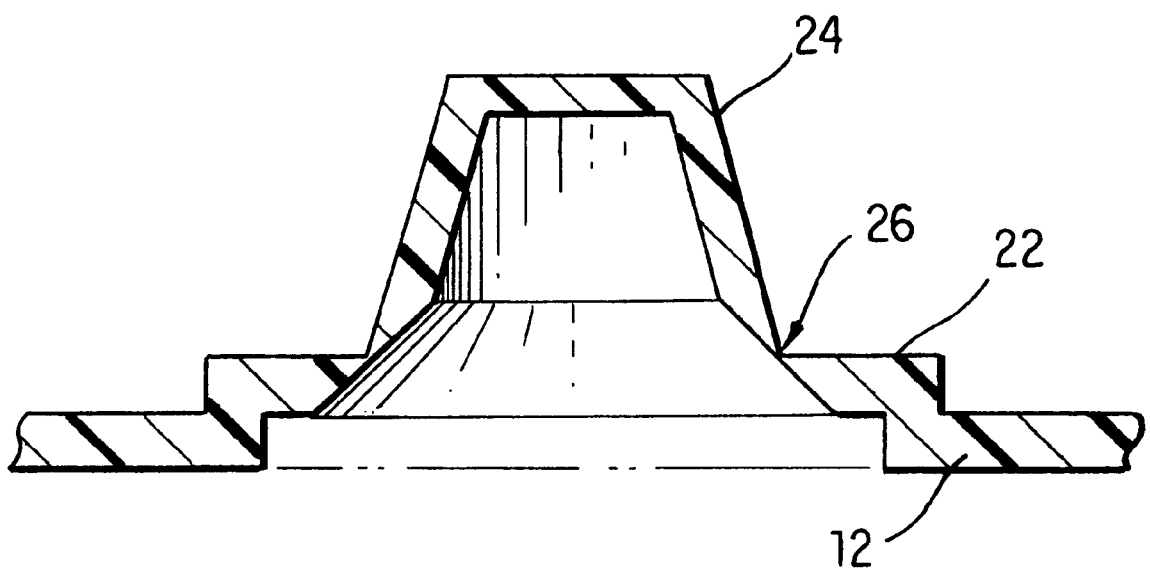
FIG. 5 is a schematic cross-section of a thermoformed plastic breakaway tip member in accordance with the present invention.

As shown in FIG. 5, the base 22 and the breakaway tip member 24 are hollow and substantially cylindrical or frusto-conical in shape. The breakaway tip member 24 is smaller than the base 22, so that, when the breakaway tip member 24 is broken from base 22, the breakaway tip member 24 may pass, fall, or be forced totally or partially through outlet opening 18 via base 22, as shown in FIG. 4. The outlet creating formation 20 is thermoformed from a plastic film, for example, polystyrene, preferably coated with a barrier material such as PVDC (Saran). As shown in the plan view of FIG. 5, the outlet creating formation 20 protrudes from the wall 12. Outlet creating formation 20 is, for illustration purposes only, shown in FIGS. 2 and 3 as protruding from wall 12 towards 14 so as to be disposed within the dispenser package. Although not specifically illustrated, it will be understood by those having ordinary skill in the art that outlet creating formation 20 may be disposed on and protruding from wall 12 in a direction away from wall 14. In either configuration, outlet creating formation 20 is disposed on the wall 12 so that, when opened, the outlet opening 18 communicates through the wall 12 and directly with the interior of the dispenser package portion (wall 12 and soft wall 14).

Outlet creating formation 20 of swab 10, as illustrated in FIGS. 2–4, 7, and 8, includes a fault line 26 intersection between the base 22 and the breakaway tip member 24. The fault line extends around the periphery of the outlet creating formation 20 at said intersection permitting the breakaway tip member 24 to be broken away from the base 22 along said fault line 26. Under the stress of sufficient applied force, as depicted, for example, in FIG. 4, the breakaway tip member 24 is broken away from the base 22 along the fault line 26 and is forced at least partially through base 22 toward sponge member 30, thus forming outlet 18 through wall 12. The breaking force applied to and breaking away the breakaway tip member 24 allows the flow of fluid contents 17 from the dispenser package, through outlet opening 18, and into the sponge member 30.

Figure 6A:
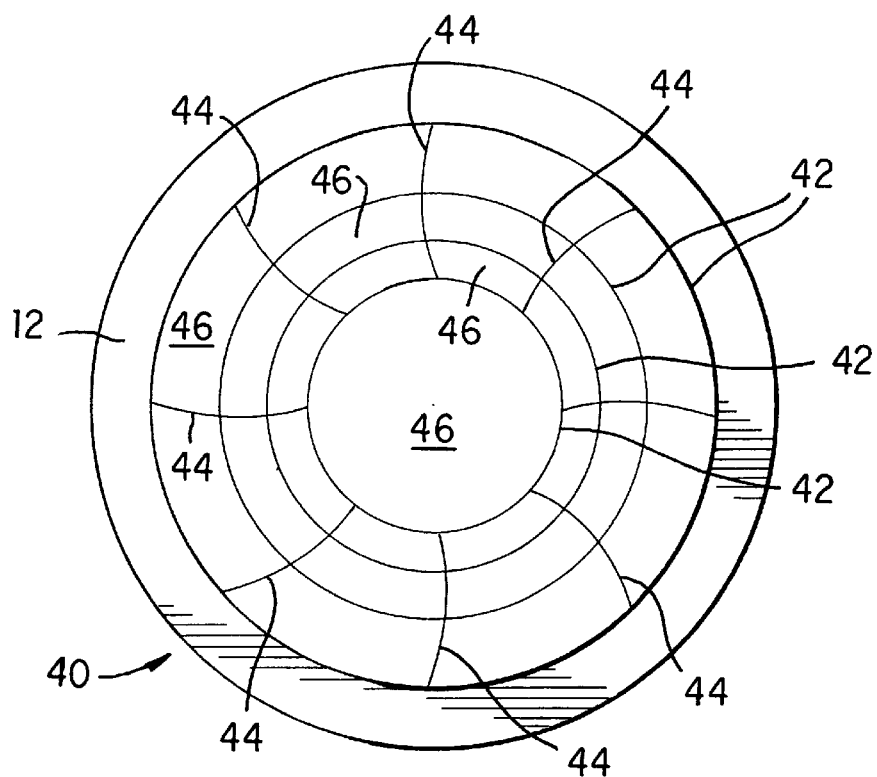
FIG. 6A is a schematic elevation view of a frangible plastic member in accordance with the present invention.
Figure 6B:
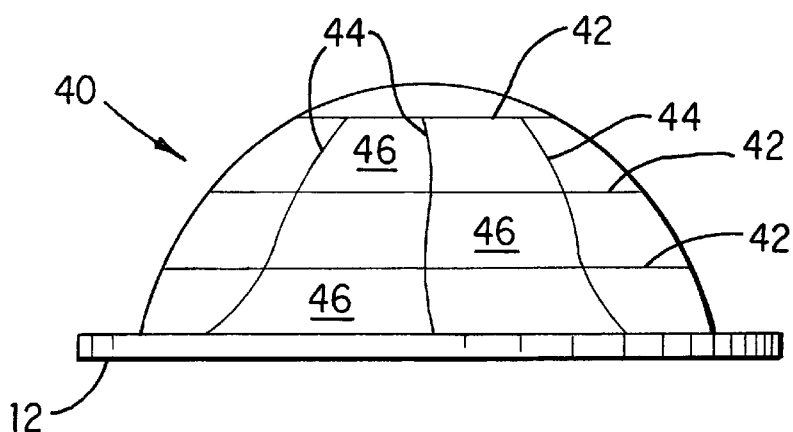
FIG. 6B is a top view of the frangible plastic member illustrated in FIG. 6A.
Figure 8A:
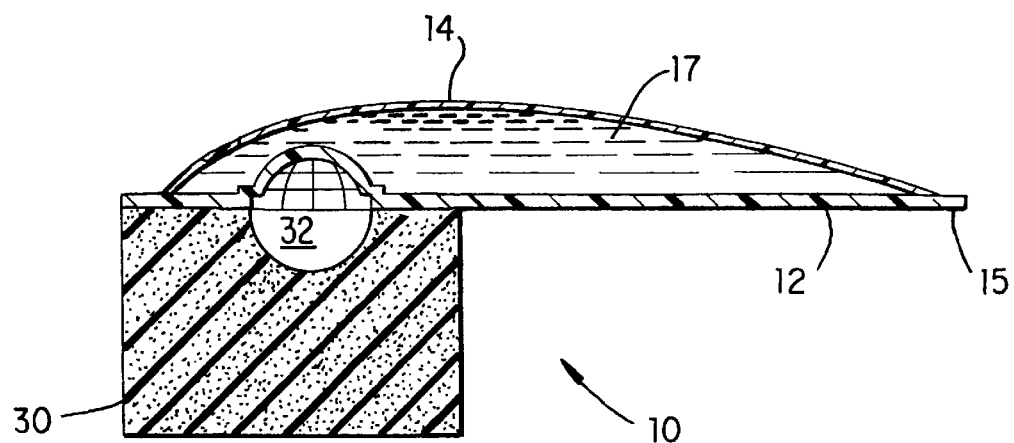
FIG. 8A is an elevated cross-sectional side view of a swab with the frangible plastic member illustrated in FIGS. 6A and 6B constructed in accordance with the present invention.
Figure 8B:
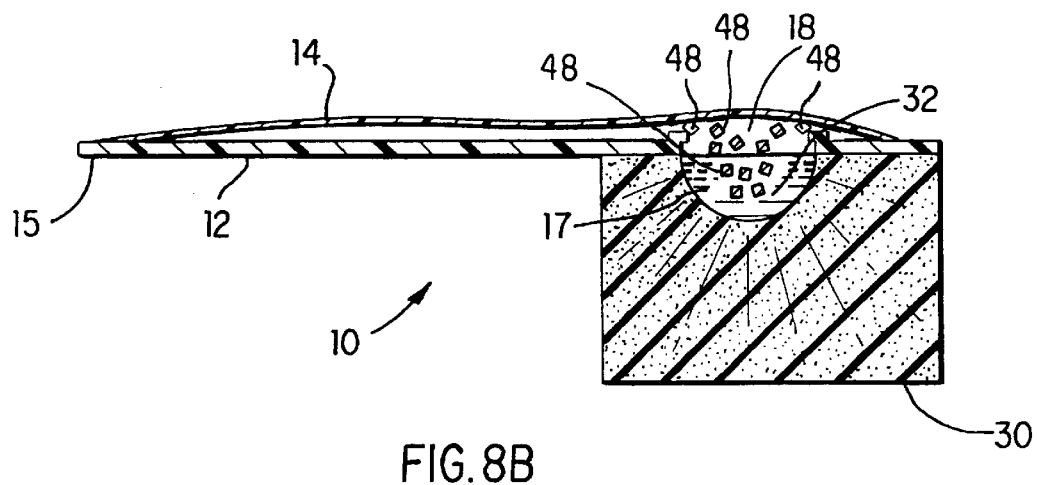
FIG. 8B is a cross-sectional side view of a swab in accordance with the present invention, with the frangible plastic member illustrated in FIGS. 6A and 6B, after a sufficient rupturing or crushing force has been applied and released.

In further accordance with the present invention as illustrated in FIGS. 6A and 6B, outlet-creating formation 20 comprises a frangible plastic member generally shown at 40. Frangible plastic member 40 comprises a hollow protrusion having a fault line pattern comprising a plurality of intersecting latitudinal and longitudinal fault lines 42 and 44, respectively. The fault line pattern, 42 and 44, segment the frangible plastic tip 40 into a plurality segments or pieces 46. FIG. 8A illustrates swab 10 constructed with the frangible plastic member 40. As illustrated in FIG. 8B, under the stress of a sufficient applied force, as depicted and referred to above, frangible plastic member 40 will be crushed and broken apart along or at least some portion of the fault line pattern, 42 and 44. It is not required that the fault lines 42 and 44 actually be partially or completely severed from the wall member 12 or that they actually be partially or completely crushed, so long as they rupture and create small apertures between some of the segments 46 allowing the fluid to saturate the sponge member 30, as shown in FIG. 8B. The crushing force applied to the frangible plastic member 40 also allows the flow of fluid contents 17 from the dispenser package, through the newly formed outlet opening 18, and into the sponge portion 30. Frangible plastic member 40 is made from the similar materials as is the base 22 and breakaway tip member 24. Additionally, latitudinal fault lines 42 and longitudinal fault lines 44, forming the fault line pattern, are similar to the fault line 26 formed at the intersection of the base 22 and the breakaway tip member 24.

Figure 9:
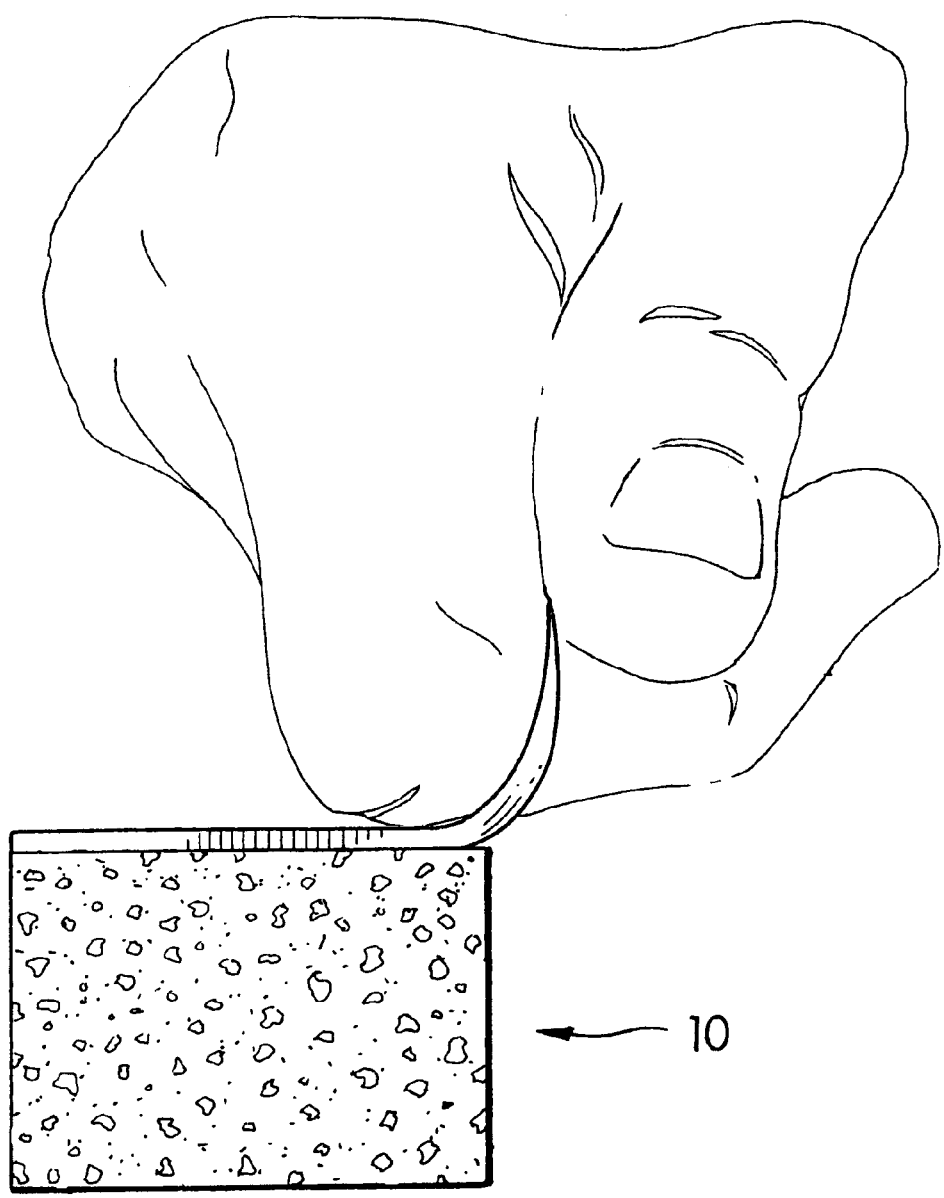
FIG. 9 is a side-view of a swab in accordance with the present invention during the application of the fluid contents to a surface.

During use, as shown in FIG. 9, swab 10 is grasped, by the hand of a user, along at least a portion of the dispenser package. The sponge member 30, saturated with the fluid contents 17, is placed in contact with the surface in which the fluid contents 17 are to be applied.

It should be understood that the outlet creating formation as well as the fault line 26 and fault line pattern may be thermoformed into any configuration and size necessary in carrying out the spirit of the invention.

Figure 10:
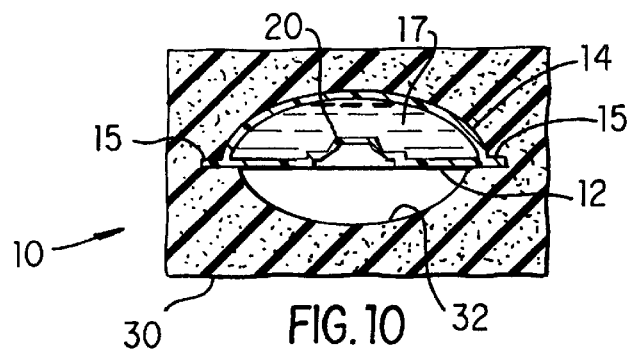
FIGS. 10, 11, and 12 are cross-sectional side views of additional swabs in accordance with the present invention.
Figure 11:
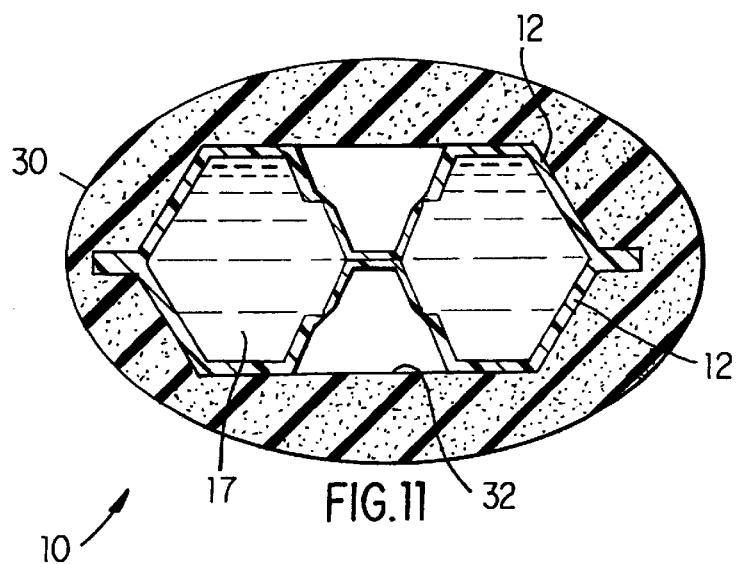
Figure 12:
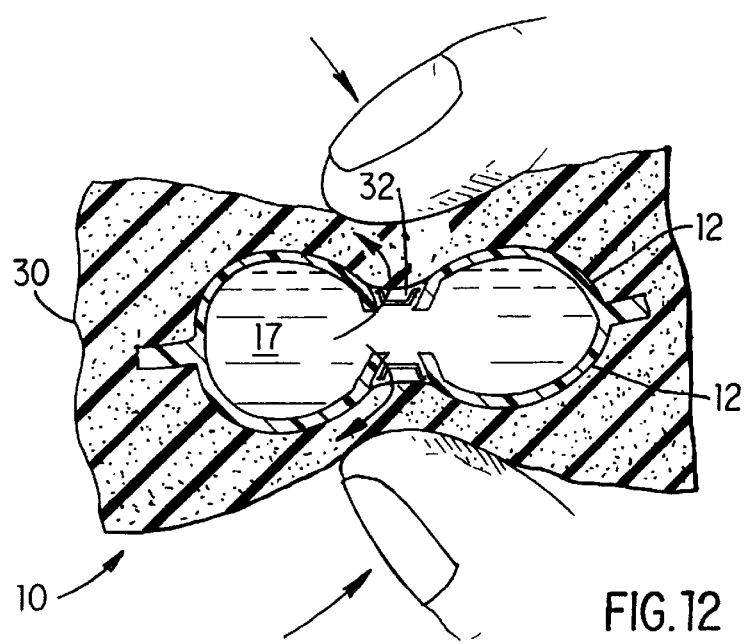

FIGS. 10, 11, and 12 illustrate alternative swab construction, wherein dispensing containers, similar to those previously described above, are completely encapsulated in a sponge member or other absorbent material by methods well known in the prior art. These alternative swab constructions are specifically suited for insertion into body cavities, e.g., the rectal cavity, in applying medication for the treating hemorrhoids, or for insertion into the vagina, in applying medications, deodorants, and/or contraceptives.

The alternative internal swab 10, as illustrated in FIG. 10, comprises a hollow dispenser container including a wall 12 and a soft wall 14 sealed together about their peripheries 15. An outlet creating formation 20, made in accordance with the structure illustrated in FIGS. 5, 6A and 6B and discussed above in detail, is disposed on wall 12. As illustrated in FIG. 4 and also in FIG. 12, a force sufficient to break or crush the outlet creating formation dispenses the fluid contents 17 from the dispenser package portion into the sponge member 30 by way of an outlet opening (not shown in FIG. 10).

The alternative internal swab 10, as illustrated in FIG. 11 comprises a dispenser package portion including at least two walls 12 made of thermoformed plastic sealed together about their peripheries. Outlet creating formations 20, are made in accordance with the structures illustrated in FIGS. 5, 6A and 6B and discussed above in detail, and disposed on each of the walls 12. The outlet creating structures are, as illustrated in FIG. 11, diametrically disposed from one another, so as when a sufficient force is applied to said internal swab 10 as discussed/above, both of the outlet creating formations are broken or crushed to form outlet openings and dispense the fluid contents 17 from the dispenser package portion, though the outlet opening, and into the sponge member 30. FIG. 12 illustrates the alternative swab 10 shown in FIG. 11, as a user applies sufficient force to break or crush the outlet creating formations and form two outlet opening for the flow of the fluid contents 17 from the dispenser package, through the outlet openings, and into the sponge member 30 or other absorbent material.

Figures 13A, 13B:
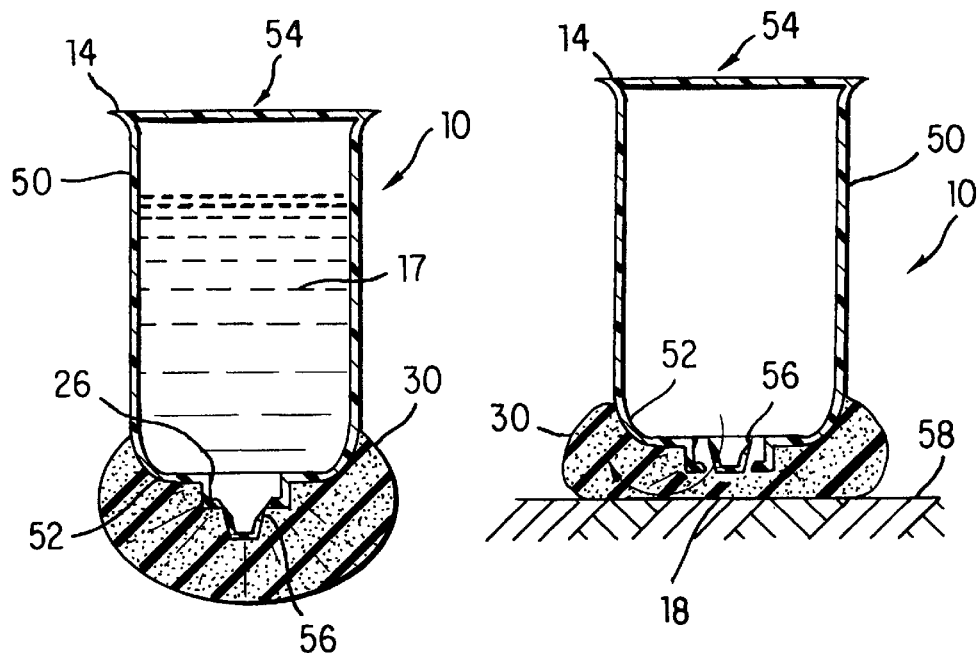
FIGS. 13A, 13B, and 13C, illustrate further swabs in accordance with the present invention.

FIGS. 13A, 13B, and 13B illustrate a further alternative swab construction wherein the dispenser container comprises a thermoformed hollow tubular member 50 having a closed end 52 and an opposing opened end 54. Closed end 52 includes a protruding, rupturable, and thermoformed hollow formation 56. The intersection between the closed end 52 and the hollow formation 56 includes a fault line 26. Fluid contents 17 may be introduced into the hollow member 50 through its opened end 54 after which the opened end 54 is sealingly closed with a soft plastic side wall 14. An absorbent sponge material 30 is adheringly attached to the hollow tubular member 50 at its closed end 52 over the protruding hollow member 56 for absorbing the fluid contents 17. Alternatively, the dispenser container may be completely enclosed in the absorbent sponge-like material 30.

In use, further alternative swab 10, as further illustrated in FIG. 13B, is pressed against a firm surface 58 which flattens the sponge member 30 and presses the tip 56 until it ruptures at the fault line 26 and breaks the hollow formation 56 to form outlet opening 18.

Figure 13C:
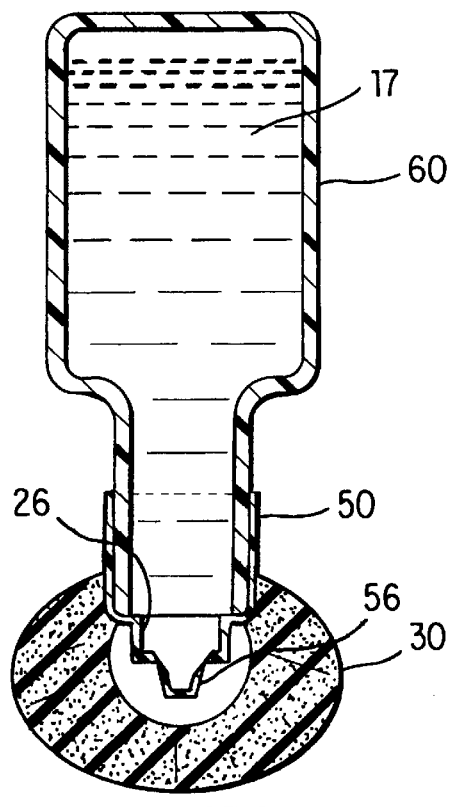

The further alternative swab 10, as illustrated in FIG. 13C, may, for example, be mated in a leak proof manner, at its opened end 54, to an additional means 60, such as a bottle of selected fluid contents 17, to extend the size and functionality of the tubular member 52.

It will remain understood by those skilled in the art that the present invention in its broader aspects is not limited to the particular embodiments shown and described herein, and that variations may be made without departing from the principles of the invention and without sacrificing its chief advantages.

I claim:

1. A dispensing container for fluid comprising a thermoformed plastic film having at least one manually controllably rupturable hollow formation exposed to a fluid contained in said container and protruding from a surface of said thermoformed plastic film, when said at least one formation is manually squeezed said at least one formation ruptures creating an outlet for said fluid to flow through said outlet and out of said container; and wherein said at least one formation is covered with an absorbent sponge-like material which when said at least one formation is ruptured will absorb said fluid flowing out of said container.

2. The dispenser of claim 1 where said dispenser container is entirely enclosed in an absorbent sponge-like material.

3. A dispensing container for fluid comprising a thermoformed plastic film having at least one manually controllably rupturable hollow formation exposed to a fluid contained in said container and protruding from a surface of said thermoformed plastic film, when said at least one formation is manually squeezed said at least one formation ruptures creating an outlet for said fluid to flow through said outlet and out of said container; and wherein said container is a two walled pouch with at least one relatively stiff side in which said at least one formation is formed, said two walls sealed peripherally to each other to create a containment pouch.

4. The dispenser of claim 3 where said at least one relatively stiff side has an absorbent sponge-like material adheringly attached to it over said at least one formation to absorb said contained fluid.

5. The dispenser of claim 1 where said container is a thermoformed hollow member with a closed end comprising said at least one formation and an opposing open end for filling said fluid after which said open end is sealingly closed.

6. A dispensing container for fluid comprising a thermoformed plastic film having at least one manually controllably rupturable hollow formation exposed to a fluid contained in said container and protruding from a surface of said thermoformed plastic film, when said at least one formation is manually squeezed said at least one formation ruptures creating an outlet for said fluid to flow through said outlet and out of said container; and wherein said container is a thermoformed generally tubular member with one closed end, said closed end comprising said at least one formation and another end being mated in a leakproof manner to an additional means to extend the size and functionality of said tubular member.

7. A dispensing container for fluid comprising a thermoformed plastic film having at least one manually controllably rupturable hollow formation exposed to a fluid contained in said container and protruding from a surface of said thermoformed plastic film, when said at least one formation is manually squeezed said at least one formation ruptures creating an outlet for said fluid to flow through said outlet and out of said container; and wherein said at least one formation comprises a breakaway tip extending from said surface wherein a locus of a line of intersection of said breakaway tip with said surface comprises a locus of a fault line.

8. The dispenser of claim 1 where said at least one formation is a hollow member whose surface contains a rupturable fault line pattern.

* * * * *

UNITED STATES PATENT AND TRADEMARK OFFICE
CERTIFICATE OF CORRECTION

PATENT NO.    : 6,536,974 B2
DATED         : March 25, 2003
INVENTOR(S)   : Sanford Redmond It is certified that error appears in the above-identified patent and that said Letters Patent is hereby corrected as shown below:

Column 2,
Line 18, "thereof The" should read -- thereof. The --.

Column 5,
Line 20, "thermoformed plastic sealed" should read -- thermoform plastic film sealed --.

Signed and Sealed this

Twenty-eighth Day of October, 2003

JAMES E. ROGAN
*Director of the United States Patent and Trademark Office*